(12) United States Patent
Draper et al.

(10) Patent No.: US 8,581,577 B2
(45) Date of Patent: Nov. 12, 2013

(54) LOW ROW STEAM GENERATOR INSPECTION PROBE

(75) Inventors: Jeffrey Bishop Draper, McVeytown, PA (US); Lance Edmund Maggy, Mount Pleasant, SC (US)

(73) Assignee: General Electric Company, Schenectady, NY (US)

( * ) Notice: Subject to any disclaimer, the term of this patent is extended or adjusted under 35 U.S.C. 154(b) by 265 days.

(21) Appl. No.: 13/173,519

(22) Filed: Jun. 30, 2011

(65) Prior Publication Data

US 2012/0007594 A1   Jan. 12, 2012

Related U.S. Application Data

(63) Continuation-in-part of application No. 13/031,905, filed on Feb. 22, 2011.

(60) Provisional application No. 61/363,554, filed on Jul. 12, 2010.

(51) Int. Cl.
*G01N 27/72* (2006.01)

(52) U.S. Cl.
USPC ........... 324/220; 324/219; 324/221; 324/238; 73/866.5; 73/865.8; 29/727

(58) Field of Classification Search
USPC .............. 324/238, 219–221; 73/865.8, 866.5; 29/727
See application file for complete search history.

(56) References Cited

U.S. PATENT DOCUMENTS

| | | | |
|---|---|---|---|
| 4,476,368 A | 10/1984 | Cammann et al. | |
| 4,821,943 A | 4/1989 | Gaudin et al. | |
| 4,918,808 A | 4/1990 | Cartry et al. | |
| 5,025,215 A | 6/1991 | Pril | |
| 5,028,381 A | 7/1991 | Dugue | |
| 5,174,164 A * | 12/1992 | Wilheim | 73/866.5 |
| 5,247,251 A * | 9/1993 | Yost et al. | 324/220 |
| 5,279,168 A | 1/1994 | Timm | |
| 5,398,560 A * | 3/1995 | Zollingger et al. | 73/865.8 |

(Continued)

FOREIGN PATENT DOCUMENTS

| | | |
|---|---|---|
| EP | 0244283 A1 | 11/1987 |
| EP | 0298841 A1 | 1/1989 |

(Continued)

OTHER PUBLICATIONS

Search Report and Written Opinion from WO Application No. PCT/US2012/025618 dated Apr. 16, 2013.
Search Report and Written Opinion from WO Application No. PCT/US2012/025616 dated Apr. 18, 2013.

*Primary Examiner* — Huy Q Phan
*Assistant Examiner* — Adam Clarke
(74) *Attorney, Agent, or Firm* — Cooper Legal Group, LLC

(57) ABSTRACT

An inspection assembly for insertion inspection of an elongate hollow member. The inspection assembly includes a probe head including at least one sensor for sensing a characteristic of the elongate hollow member as the probe head is moved internally within the elongate hollow member. The assembly includes a flexible shaft connected to the probe head and transmitting a motive force to the probe head to move the probe head within the elongate hollow member. The flexible shaft encloses at least one wire operatively connected between the probe head and at least one component external to the elongate hollow member for sensory operation of the at least one sensor. The flexible shaft is at least partially corrugated.

4 Claims, 4 Drawing Sheets

(56) References Cited

U.S. PATENT DOCUMENTS

| | | |
|---|---|---|
| 7,109,704 B1 * | 9/2006 | Loud .............................. 324/262 |
| 2004/0257072 A1 * | 12/2004 | Samson ......................... 324/242 |
| 2008/0278157 A1 | 11/2008 | Zimmerman |
| 2011/0089937 A1 | 4/2011 | Petrosky |
| 2012/0006134 A1 * | 1/2012 | Draper et al. ................ 73/866.5 |
| 2013/0009634 A1 | 1/2013 | Lakhan et al. |

FOREIGN PATENT DOCUMENTS

| | | |
|---|---|---|
| EP | 0354090 A2 | 2/1990 |
| FR | 2928024 A1 | 8/2009 |
| WO | 9313413 A1 | 7/1993 |
| WO | 2010148487 A1 | 12/2010 |

* cited by examiner

LOW ROW STEAM GENERATOR INSPECTION PROBE

CROSS REFERENCE TO RELATED APPLICATION

The present application is a continuation of U.S. Provisional Patent Application No. 61/363,554, filed Jul. 12, 2010, and is a continuation in part of U.S. patent application Ser. No. 13/031,905, filed Feb. 22, 2011, both of which are incorporated herein by reference.

BACKGROUND OF THE INVENTION

1. Field of Invention

The present invention relates to internal inspection probes for inspecting hollow members, such as a hollow member present within nuclear steam generator.

2. Discussion of Prior Art

Use of inspection/detection devices, such as eddy current sensors, is known. Such devices can be used, for example, for nuclear generator hollow tubular members with tortuous bends (e.g., u-bends). However, it is possible know devices to become lodged, or otherwise not able to proceed along the hollow member such that further inspection is not possible. Thus there is a need for improvements to avoid such issues.

BRIEF DESCRIPTION OF THE INVENTION

The following summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

In accordance with an aspect, the present invention provides an inspection assembly for insertion inspection of an elongate hollow member. The inspection assembly includes a probe head including at least one sensor for sensing a characteristic of the elongate hollow member as the probe head is moved internally within the elongate hollow member. The assembly includes a flexible shaft connected to the probe head and transmitting a motive force to the probe head to move the probe head within the elongate hollow member. The flexible shaft encloses at least one wire operatively connected between the probe head and at least one component external to the elongate hollow member for sensory operation of the at least one sensor. The flexible shaft is at least partially corrugated.

BRIEF DESCRIPTION OF THE DRAWINGS

The foregoing and other aspects of the invention will become apparent to those skilled in the art to which the invention relates upon reading the following description with reference to the accompanying drawings, in which.

DETAILED DESCRIPTION OF THE INVENTION

Figure 1:
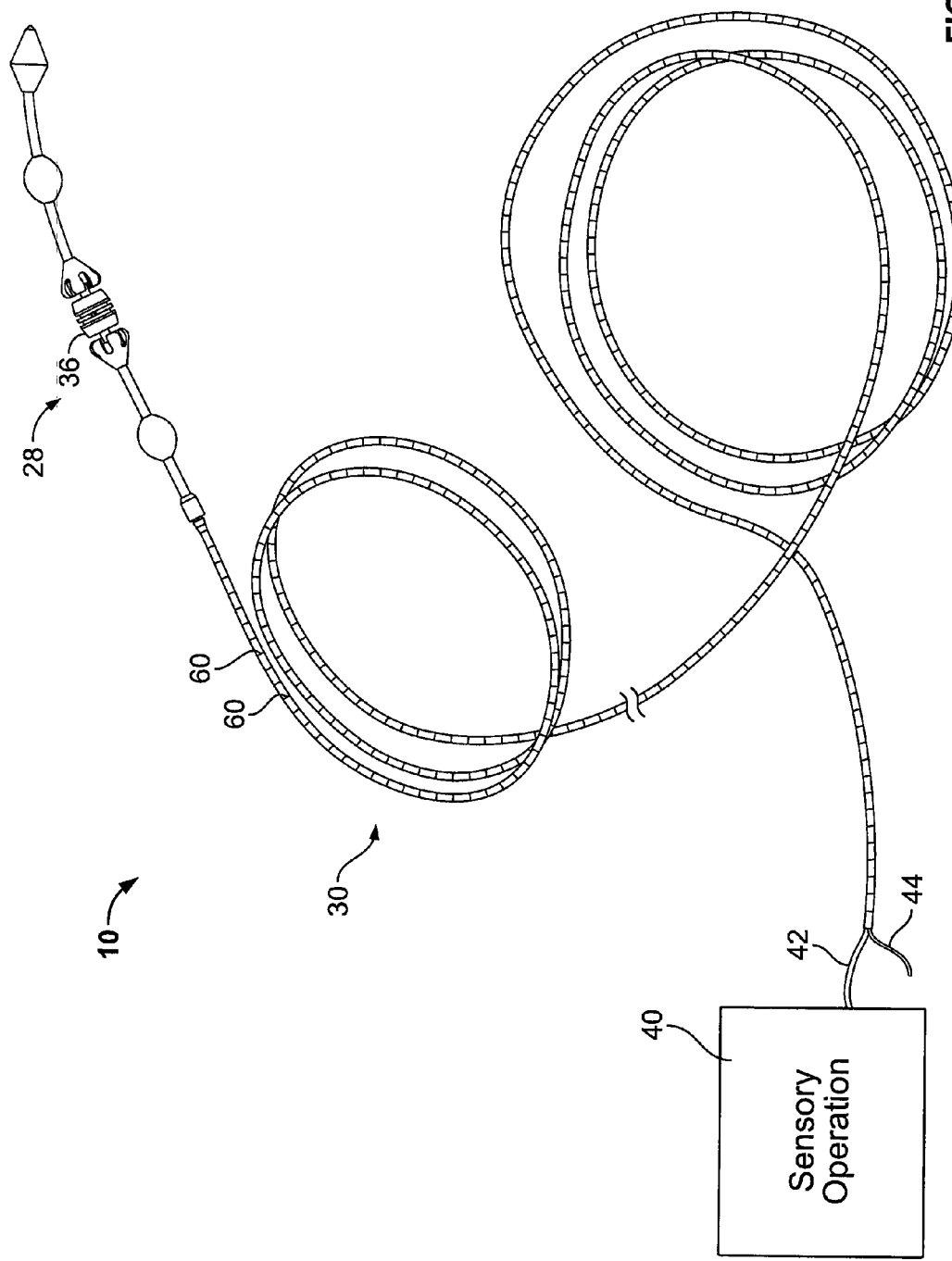
FIG. 1 is a schematized illustration of an example inspection assembly in accordance with at least one an aspect of the present invention.

Illustrative embodiments that incorporate one or more aspects of the invention are described and illustrated in the drawings. These illustrated examples are not intended to be overall limitations on the invention. For example, one or more aspects of the invention can be utilized in other embodiments and even other types of devices. Moreover, certain terminology is used herein for convenience only and is not to be taken as a limitation on the invention. Still further, in the drawings, the same reference numerals are employed for designating the same elements.

An example of an inspection assembly 10 in accordance with aspects of the present invention is schematically shown in FIG. 1. It is to be appreciated that the example is for illustrative purposes only and need not present specific limitations upon the scope of the present invention. The inspection assembly 10 is for insertion inspection of an elongate hollow tubular member 12 (see for example, a tubular member shown within FIG. 2).

Figure 2:
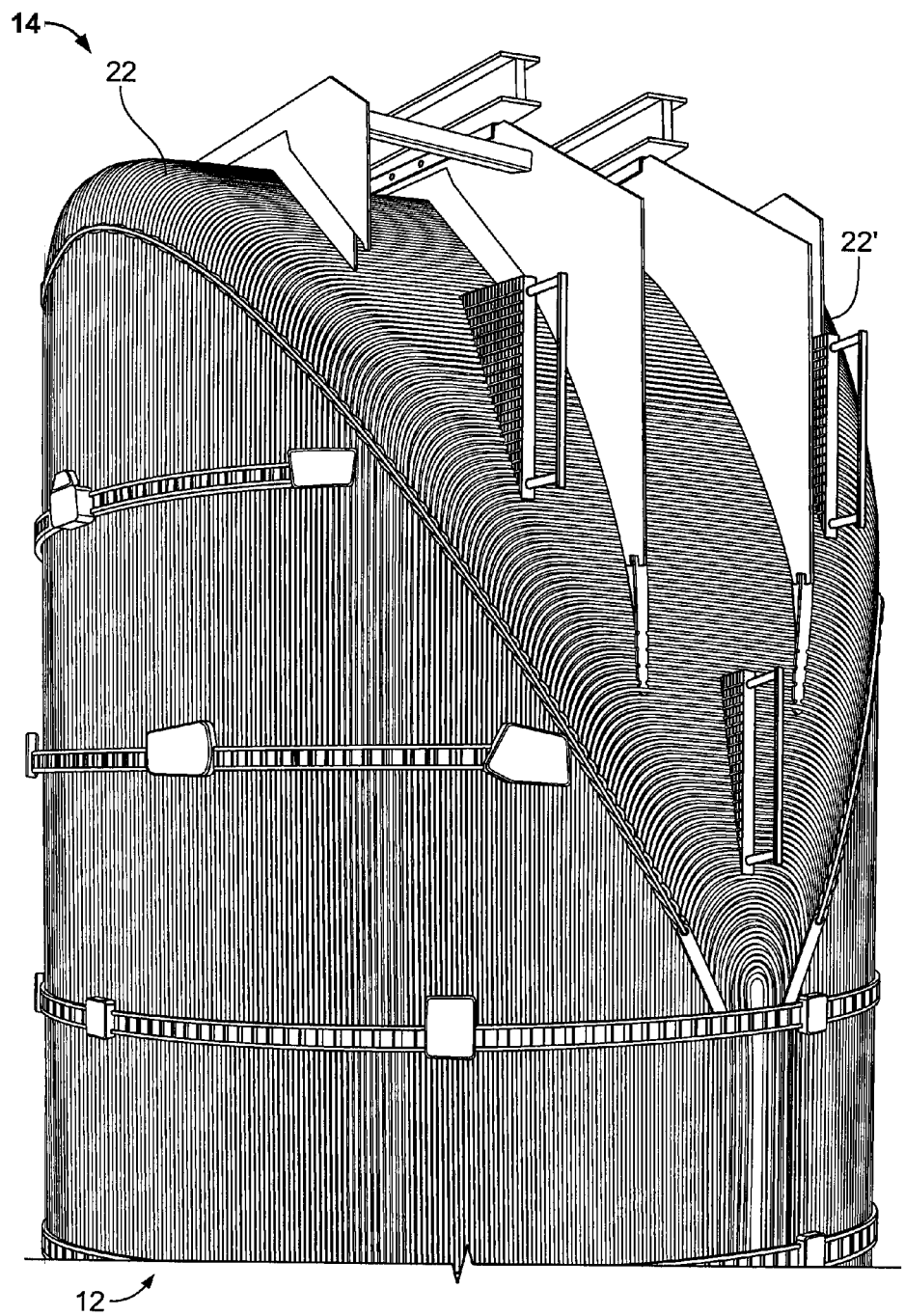
FIG. 2 is an illustration of an example of a nuclear steam generator having a plurality of hollow members that have at least one bend and within which the present invention may be utilized.

The device shown in FIG. 2 is an example generator 14 within which the inspection assembly 10 of FIG. 1 may be utilized. The tubular member 12 may be part of a "Low Row" (2.0" radius tube and greater) U-bend tube of the generator 14. The example generator 14 shown within FIG. 2 merely presents one example environment for the inspection assembly 10. It is to be appreciated that the present invention can be used in other environments (e.g., other tubular environments associated with different generators and other tubular environments that are not part of a generator). The generator 14 and numerous tubular members 12 (only one example tubular member 12 is identified with a reference number, however, any of the shown tubular members could be so identified).

Figure 3:
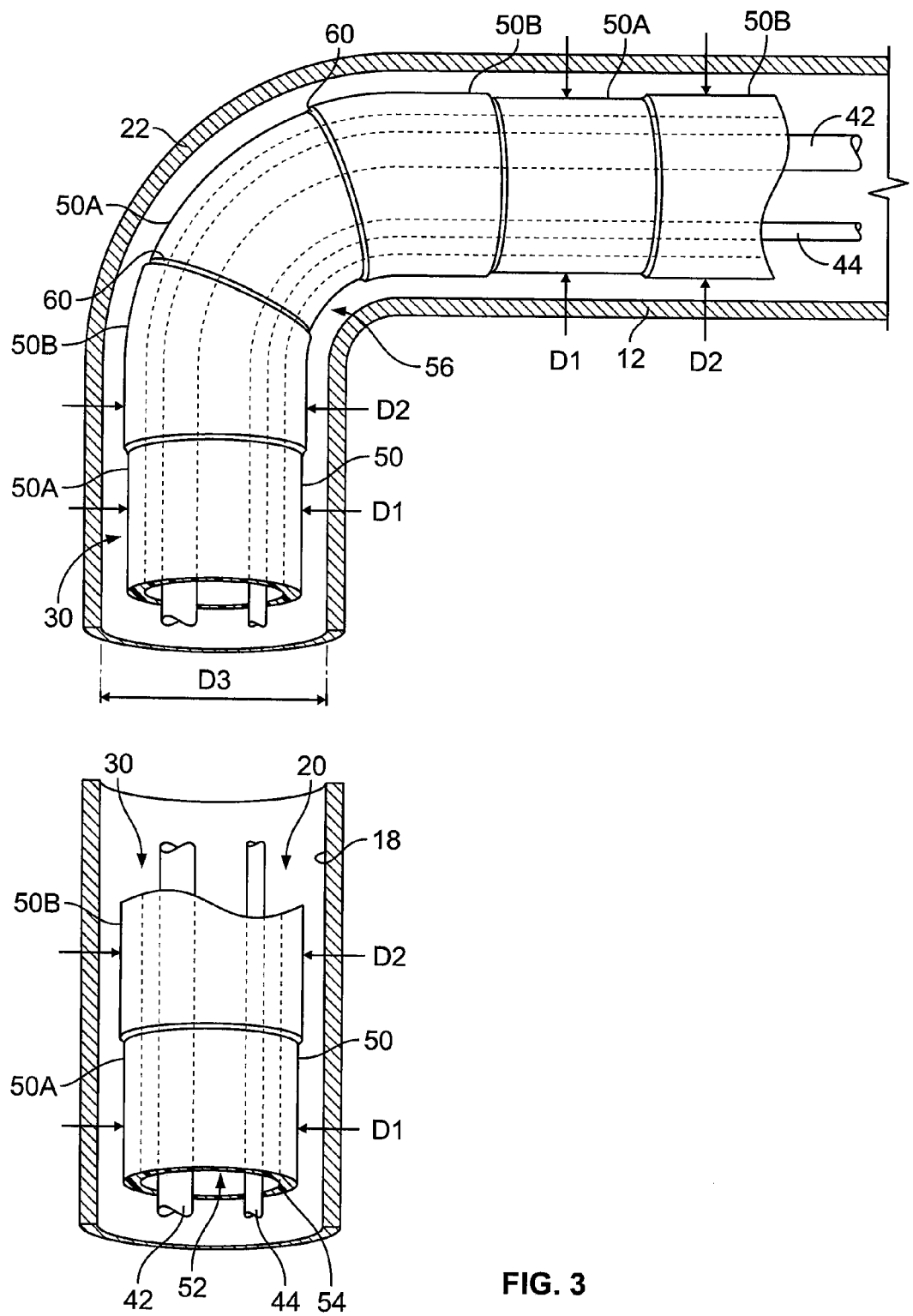
FIG. 3 is an illustration of torn-away portions of an example probe shaft of the assembly of FIG. 1 that are within example torn-open portions of a hollow member of the generator of FIG. 2 and in accordance with at least one aspect of the present invention.

Focusing upon the tubular member 12, the tubular member is hollow and has a generally arcuate/rounded (e.g., circular or oval cross-section) interior surface 18 (see the example section of FIG. 3). The interior surface 18 of the tubular member 12 bounds an interior space 20 of the tubular member 12. In some specific examples the tubular member 12 is relatively long and has at least one bend 22 (the example bend shown in FIG. 2 is a transition between vertical and horizontal sections of the tubular member). In further specific examples, the tubular member 12 has multiple bends (e.g., 22' shown within FIG. 2) and thus provides a tortuous path along its interior space 20. In at least one example, two bends 22, 22' within the tubular member 12 provides the member with a U-bend configuration. The tubular member 12 can have a varied length. The at least one bend 22 and/or the length of the tubular member 12 can provide for a path within the tubular member that can be considered to be tortuous.

Focusing again upon the inspection assembly 10 (FIG. 1), the assembly is for inspection of the tubular member 12 (FIGS. 2 and 3) from the perspective of the interior space 20 of the tubular member 12. Such inspection may be in the form of sensing/testing/monitoring at least one condition of the tubular member 12 from the interior space 20 of the tubular member along the tubular member. The at least one condition need not be a specific limitation upon the present invention. The inspection assembly 10 (FIG. 1) includes a probe head 28 and a flexible probe shaft 30, with the probe head 28 connected to the probe shaft 30.

At least one sensor 36 (shown generically in FIG. 1) that senses/tests/monitors the at least one characteristic (e.g., a condition) of the tubular member 12 is located within/at the probe head 28. The type/specifics of the sensor(s) 36 within the probe head 28, and the probe head 28 itself, need not be specific limitations upon the present invention. An example of characteristic (e.g., a condition) to be sensed/tested/monitored includes structural integrity (e.g., weakened portions) of the tubular member 12. In one example, the sensor(s) 36 include an eddy current sensor that includes wire windings within a bobbin and an adjacent magnet. It is to be appreciated that the probe head 28 may include a variety of structures, components, features, and the like that need not be part of the present invention. The other components may or may not be spaced apart upon a flexible segment. As such, the probe head 28 shown within FIG. 1 is merely an example.

The probe head 28 is operatively connected to a sensory operation portion 40 (schematically represented as simply a box) of the inspection assembly 10 via at least one wire 42. To be cleat; the wire(s) 42 may be a plurality of wires or provided as a wiring bundle and referred to as a simply a wire. Different wires within the plurality or bundle could accomplish different functions. The wires) 42 extends to be operatively connected to the probe head 28, extends along the length of the probe shaft 30, and extends to be operatively connected to the sensory operation portion 40. The wire(s) 42 are housed within an interior of the probe shaft 30 as described further following. Electrical power and/or electrical signals (e.g., control and/or sensory) are passed along the wire(s) 42 between the probe head 28 and the sensory operation portion 40.

In general, the probe head 28 of the inspection assembly 10 is moved along the interior space 20 of the tubular member 12 while the probe head 28 senses/tests/monitors. The sensory operation portion 40, via the wire connection to the probe head 28, provides power and/or control and receives sensory signals from the probe head 28 to make determination(s) about the sensed/tested/monitored at least one condition of the tubular member 12 as the probe head 28 is moved relatively along the tubular member. In is to be appreciated that the sensory operation portion 40 may contain any suitable structures to perform the functions, such as power source components, processing components (e.g., one or more microprocessors), data storage components, and communication components. The sensory operation portion 40 may be operatively connected to one or more external or intermediary components (not shown) for control of the sensory operation portion 40 and/or provision of the sensory information outside of the shown system and/or other operations.

As mentioned, the probe head 28, with its sensor(s) 36, is moved along the tubular member 12. The movement along the tubular member 12 is first inbound (e.g., inserting) relative to the tubular member 12 and is secondly outbound (e.g., extracting) relative to the tubular shaft. The motive force to move the probe head 28 along tubular member 12 is imparted via force applied to the probe shaft 30. In one example, the motive force is in the form of manual force applied to the probe shaft 30.

As mentioned, the probe shaft 30 houses the wire(s) 42 extending between the probe head 28 and the sensory operation portion 40. It is possible to consider the wire(s) 42 to be part of the probe shaft 30. Also, within the shown example, an optional non-metal cable 44 is provided as part of the probe shaft 30, and the cable is coupled to the probe head 28. The cable 44 is housed within the interior of the probe shaft 30 and can be considered to be part of the probe shaft. The cable 44 provides for the transmission of tensile force for extracting (i.e., pulling to retrieve) the probe head 28 from the tubular member 12. The cable 44 may be braided filament cordage. The use of non-metal material for the cable 44 helps to avoid imposing electrical interference to the wire(s) 42. Of course, a different construction/material may be used for the cable 44.

Focusing upon the probe shaft 30, the shaft includes a surrounding, hollow sheath tubing 50 that houses and encloses the wire(s) 42 and the optional cable 44 within an interior space 52 of the sheath tubing 50. The sheath tubing may be made of a polymer material. Within the shown example, the tubing 50 is a one-piece, continuous and monolithic member. Also within the shown example, the one-piece, continuous and monolithic tubing 50 extends along the entire length of the shaft 30. In other words, the tubing 50 is not composed of coupled parts within this example. However, as shown within another example, it is possible to construct a composite shaft via the use of coupled, multiple parts.

The interior space 52 of the sheath tubing 50 is bounded by an interior surface (or surface segments) 54 of the sheath tubing 50. The cross-sectional area of the interior space 52 may be any suitable cross-section dimension for acceptance of the wire(s) 42 and optional cable 44 therein. It is possible that the cross-sectional size of the interior space 52 may vary along its length. It is to be noted that FIG. 3 shows the wire(s) 42 and the cable 44 filling only part of the volume of the sheath tubing. Such is only an example and permits ease of viewing the different components, and should not be taken as a required limitation upon the present invention. It is certainly possible that the wire(s) 42 and the cable 44 fill the volume of the sheath tubing, and such is presented within a following discussion.

The overall length of the probe shaft 30, and specifically the sheath tubing 50, may be any suitable length. However, within one example the length is sufficiently long to meet or exceed a length measured along the entire elongate extent of the tubular member 12. For such an example, the probe head 28 may be moved along the entire elongate extent of the tubular member via insertion movement of the probe shaft 30 into the tubular member 12. Recall that it is force applied to the sheath tubing 50 of the probe shaft 30 that moves the probe head 28 along the insertion direction of the tubular member. With regard to length of the wire(s) 42, the length is of course at least a great as the sheath tubing 50, but also sufficiently long to be operatively connected to the sensory operation portion 40. With regard to length of the cable 44, the length is of course at least as great as the sheath tubing 50, but also sufficiently long to be engaged (e.g., grasped) for application of tensile (i.e., pulling) force for extracting to retrieve the probe shaft 30 and probe head 28.

The probe shaft 30, with the included wire(s) 42 and cable 44, is flexible. The flexibility allows the probe shaft 30 to proceed along bends (e.g., 22, 22') of the tubular member 12. Yet the probe shaft 30 has sufficient rigidity to allow insertion into the tubular member 12 and move the probe head 28 along the extent of the tubular member 12.

In accordance with one aspect, probe shaft 30 includes at least one feature or means for improving ease of moving the probe shaft 30 and the probe head 28 of the inspection assembly 10 along the tubular member 12. Such at least one feature or means may include reducing friction that otherwise may occur between the probe shaft 30 and the tubular member 12 and/or negotiating the torturous path of the tubular member 12.

Within one specific example, the probe shaft 30 has corrugations 60, as a structural feature or means, on its exterior. It is to be appreciated that the corrugations 60 on the probe shaft 30 may provide for improving the ease of movement and are thus an example means for improving the ease of movement. Within the shown example, the corrugations 60 are present along the entire extent of the probe shaft 30. However, it is to be appreciated that the corrugations 60 may only be present along a portion of the entire extent of the probe shaft 30. Also within the shown example, the corrugations 60 are at generally evenly spaced intervals along the probe shaft 30. However, the corrugations 60 may be at varied intervals (e.g., a greater number of corrugations 60 or a shorter spacing interval between adjacent corrugations near the probe head 28). The corrugations 60 can be any series of localized deformations, crimpings, undulations, flexing/elongation points, or the like. In one example, the corrugation can be implemented by crimping to plastically deform the sheath tubing 50 at a series of locations along its length. In another example, the corrugations are formed via molding, forming or the like.

One example of the corrugations 60 on probe shaft 30 is shown in FIG. 3. Within the shown example, the corrugations 60 are on the sheath tubing 50. In other words, the sheath tubing 50 of probe shaft 30 is corrugated (i.e., has the corrugations 60). Associated with the example corrugations 60, the exterior of the sheath tubing 50 of the probe shaft 30 has segments 50A and 50B that have alternating diameter thicknesses. Within the shown example of FIG. 3, the diameter D1 at the segments 50A is smaller than the diameter D2 at the segments 50B. Thus, the shaft segments 50A and 50B alternate to have respectively smaller and respectively larger diameters. It should be noted that the values of D1 and D2 are both smaller that the value of the diameter D3, which is the interior diameter D3 of the tubular member 12. It should be further noted that the values, relationships, etc. of the dimension D1, D2 and D3 shown within FIG. 3 are only examples and may differ and may be exaggerated for illustrative purposes.

The different diameters D1 and D2 of the alternating segments 50A and 50B may be attendant with the creation of the corrugations. Moreover, it is possible to consider the alternation of the diameters to be considered to be the corrugation. Also, it should be appreciated that there may be some variation of the diameter D1 or D2 at the segments 50A and 50B, respectively, along the extent of the sheath tubing 50 of the probe shaft 30. It should be appreciated that the alternation of segments 50A and 50B, is to provide alternation of relatively smaller and relatively greater diameter segments. Still further, although the alternation is between segments with two different diameters, it is possible to have segments of a different number of diameters.

It is contemplated that the corrugations 60 lower the contact area between the probe shaft 30 and the tubular member 12, which reduces friction. It is also contemplated that the corrugations 60 also appears to help make the probe shaft 30 more flexible, thus helping it traverse a bend 22 more easily. Turning to the specific example shown in FIG. 3, it contemplated that the segments 50A and 50B provided a function of reducing an overall amount of contact between the probe shaft 30 and the interior surface 18 of the tubular member 12. For example, the relatively larger diameter segments 50B may help to reduce (e.g., avoid) the contact between the relatively smaller diameter segments 50A and the interior surface 18 of the tubular member 12. Such reduced contact should provide for reduced friction between the probe shaft 30 and the tubular member 12.

It is also contemplated that the presence of the corrugations 60 may have other benefits. For example, the corrugations 60 may provide for a better ability to grasp and transmit force to the probe shaft 30. Such ability may be useful during insertion/extraction of the probe shaft 30 relative to the tubular member 12. Also, if a mechanized device is used for insertion/extraction of the probe shaft 30 relative to the tubular member 12, the corrugations 60 may provide for better traction by items such as pushing wheels or pushing tracks. Such better traction may help reduce slippage and increases probe shaft life.

Figure 4:
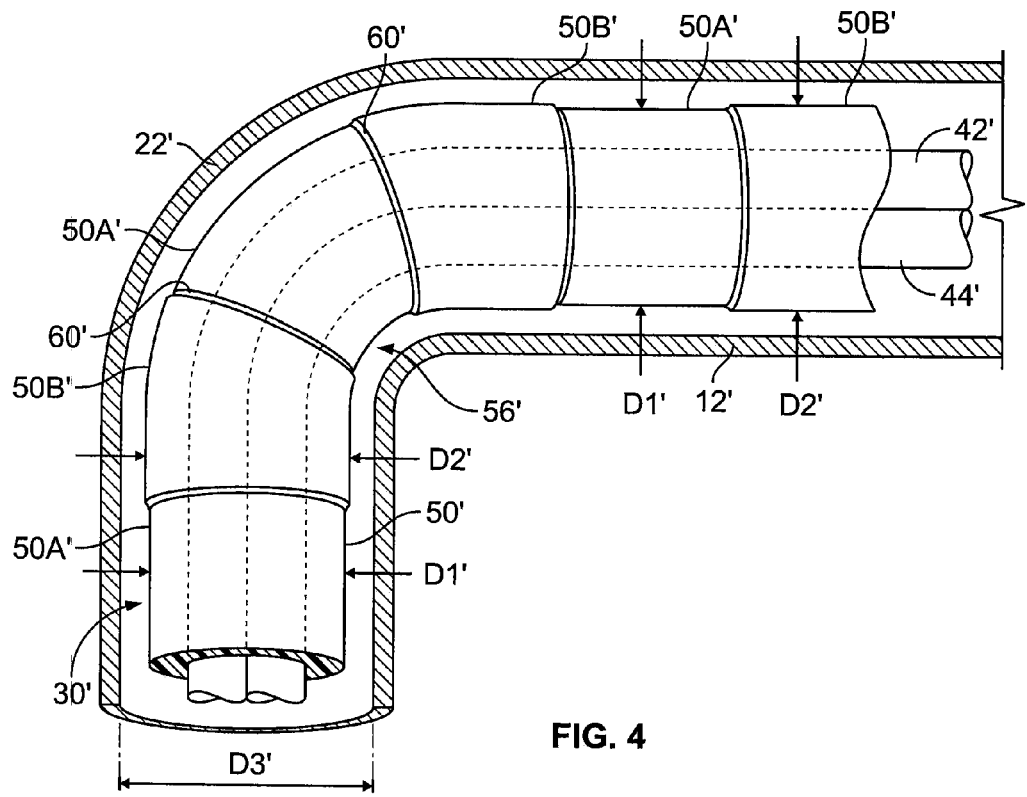
FIG. 4 is view similar to FIG. 3, but shows a torn away portion of a probe shaft of another example inspection assembly in accordance with an aspect of the present invention.

It is contemplated that changes and/or modifications can be accomplished without leaving the scope of the present invention. An example is presented within FIG. 4, which is a segment of a flexible probe shaft 30' within a segment of am elongate tubular member 12'. For ease and efficiency of understanding, structures that are generally similar to previously described structures are identified via similar numbers, but with the numbers including "'" (prime). The example of FIG. 4 shows a modification in which the probe shaft 30' does not include a hollow sheath tubing. Instead, the probe shaft 30' may be provided as a sheath encasement 50' with which at least one wire 42' is built-in and enclosed. Such can be considered to provide a single shaft. In general, the probe shaft 30 does not include an interior space and the shaft 30' can be considered solid. The shown example includes an optional cable 44'. Nonetheless, the probe shaft has series of alternating segments 50A' and 50B', which have relatively smaller and relatively greater diameters D1' and D2', respectively.

Figure 5:
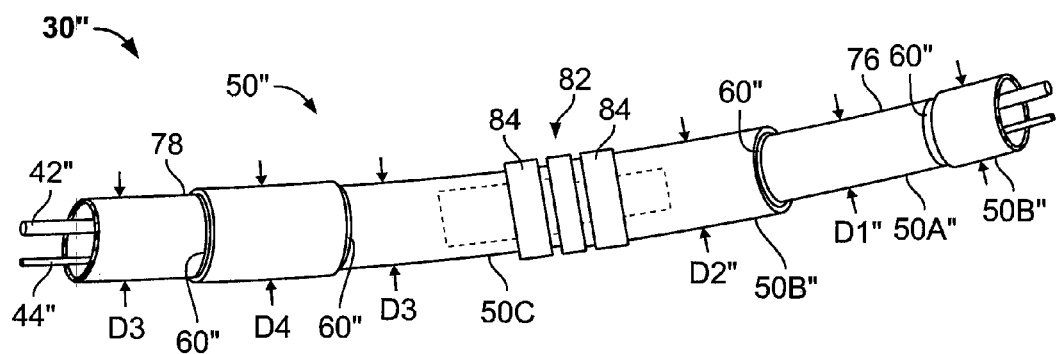
FIG. 5 is an illustration of a torn-away portion of an example probe shaft of another example inspection assembly in accordance with an aspect of the present invention in accordance with an aspect of the present invention.

Another example modification is presented within FIG. 5, which shows a segment of a probe shaft 30". For ease and efficiency of understanding, structures that are generally similar to previously described structures are identified via similar numbers, but with the numbers including "''" (double prime). Within this example, the probe shaft 30" is a composite shaft, with multiple parts. The example has two parts 76, 78 that are joined together with a coupling 82. However, it is to be appreciated that it is possible to prepare/define/provide the two parts 76, 78 via a different approach (e.g., process and/or provide treatment to one part different than the other part).

The coupling 82 is secured to the two segments via any suitable connection means 84, such as adhesive, friction engagement, crimping members or the like. It is to be appreciated that the coupling 82 is only schematically shown and thus may have a variety of constructions/configurations. Within the shown example, the coupling 82 has a hollow bore to permit passage of the wire(s) 42" and an optional cable 44".

It is to be appreciated that the lengths of the first and second parts 76, 78 can be varied. It is possible that the two parts 76, 78 (first and second parts) that have at least one dissimilarity. Examples of such dissimilarity may include diameter thickness, materials, etc. Such dissimilarity may provide for improving ease of moving.

Even though the probe shaft 30' has two parts 76 and 78, the two parts each have some corrugations 60". The corrugations 60" may be present upon all or part of the respective extents of the two parts 76 and 78. The first part 76 has alternating segments 50A" and 50B" that have relatively smaller and relatively greater diameters D1' and D2', respectively. Similarly, the second part 78 has alternating segments 50C and 50D have relatively smaller and relatively greater diameters D3 and D4, respectively. It should be appreciated that the identified diameters D1" and D2" of the first part 76 may or may not have a relationship to the identified diameters D3 and D4 of the second part 78.

In recap, the present invention provides aspects such as an inspection assembly for insertion inspection of an elongate hollow member. The inspection assembly includes a probe head including at least one sensor for sensing a characteristic of the elongate hollow member as the probe head is moved internally within the elongate hollow member. The assembly includes a flexible shaft connected to the probe head and transmitting a motive force to the probe head to move the probe head within the elongate hollow member. The flexible shaft encloses at least one wire operatively connected between the probe head and at least one component external to the elongate hollow member for sensory operation of the at least one sensor. The flexible shaft is at least partially corrugated.

Some additional aspects include that the flexible shaft can have a length extending between the probe head and a location external to the elongate hollow member and that the flexible shaft can have corrugations spaced along the entire length. The flexible shaft can include an outer tubing that extends along the entire length of the flexible shaft and is a one-piece, continuous and monolithic member. The corrugations on the flexible shaft can bound shaft segments that have differing diameters. The shaft segments can alternate to have respectively smaller and respectively larger diameters. The flexible shaft can be made of a polymer material.

The various aspects presented herein can provide for improving an ability to follow a torturous path of the elongate tubular member 12 and for aiding in kink prevention of the flexible shaft 30.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed:

1. An inspection assembly for insertion inspection of an elongate hollow member, the inspection assembly including:
    a probe head including at least one sensor for sensing a characteristic of the elongate hollow member as the probe head is moved internally within the elongate hollow member; and
    a flexible shaft connected to the probe head and transmitting a motive force to the probe head to move the probe head within the elongate hollow member, the flexible shaft enclosing at least one wire operatively connected between the probe head and at least one component external to the elongate hollow member for sensory operation of the at least one sensor, wherein the flexible shaft having a length extending between the probe head and a location external to the elongate hollow member, the flexible shaft including an outer tubing that extends along the entire length of the flexible shaft and is a one-piece, continuous and monolithic member, the flexible shaft having corrugations spaced along the entire length.

2. An inspection assembly as set forth in claim 1, wherein corrugations on the flexible shaft bound shaft segments that have differing diameters.

3. An inspection assembly as set forth in claim 2, wherein the shaft segments alternate to have respectively smaller and respectively larger diameters.

4. An inspection assembly as set forth in claim 1, wherein the flexible shaft is made of a polymer material.

* * * * *

UNITED STATES PATENT AND TRADEMARK OFFICE
CERTIFICATE OF CORRECTION

PATENT NO.        : 8,581,577 B2
APPLICATION NO.   : 13/173519
DATED             : November 12, 2013
INVENTOR(S)       : Jeffrey Bishop Draper et al.

Page 1 of 1

It is certified that error appears in the above-identified patent and that said Letters Patent is hereby corrected as shown below:

In the Specification

Column 3, Line 30

Delete "wires" and insert therefore --wire(s)--

Signed and Sealed this
Fifteenth Day of April, 2014

Michelle K. Lee
*Deputy Director of the United States Patent and Trademark Office*